US012236536B2

(12) United States Patent
Nevins et al.

(10) Patent No.: US 12,236,536 B2
(45) Date of Patent: Feb. 25, 2025

(54) SYSTEM AND METHOD FOR LOCATION DETERMINATION USING A MIXED REALITY DEVICE AND A 3D SPATIAL MAPPING CAMERA

(71) Applicants: Russell Todd Nevins, Las Vegas, NV (US); David Jon Backstein, Toronto (CA); Bradley H. Nathan, Toronto (CA)

(72) Inventors: Russell Todd Nevins, Las Vegas, NV (US); David Jon Backstein, Toronto (CA); Bradley H. Nathan, Toronto (CA)

(73) Assignees: Russell Todd Nevins, Las Vegas, NV (US); David Jon Backstein, Bonita Beach, FL (US); Bradley H. Nathan, Ontario (CA)

( * ) Notice: Subject to any disclaimer, the term of this patent is extended or adjusted under 35 U.S.C. 154(b) by 0 days.

(21) Appl. No.: 17/486,677

(22) Filed: Sep. 27, 2021

(65) Prior Publication Data

US 2022/0051483 A1    Feb. 17, 2022

Related U.S. Application Data

(63) Continuation of application No. 17/473,867, filed on Sep. 13, 2021, which is a continuation of application
(Continued)

(51) Int. Cl.
*G06T 19/00* (2011.01)
*A61B 34/10* (2016.01)
(Continued)

(52) U.S. Cl.
CPC ............ *G06T 19/006* (2013.01); *A61B 34/10* (2016.02); *A61B 90/92* (2016.02); *G06F 3/0304* (2013.01);
(Continued)

(58) Field of Classification Search
None
See application file for complete search history.

(56) References Cited

U.S. PATENT DOCUMENTS 7,331,929 B2    2/2008  Morita et al.
7,812,815 B2   10/2010  Banerjee
(Continued)

FOREIGN PATENT DOCUMENTS

CN    107430437 A    12/2017
CN    110430809 A    11/2019
(Continued)

OTHER PUBLICATIONS

Microsoft HoloLens & Mixed /Reality Healthcare Industry Deck, unknown author, at least as early as Oct. 14, 2019.
(Continued)

*Primary Examiner* — Kyle Zhai
(74) *Attorney, Agent, or Firm* — MORRISS O'BRYANT COMPAGNI CANNON, PLLC

(57) ABSTRACT

A system and method for determining a location for a surgical jig in a surgical procedure includes providing a mixed reality headset, a 3D spatial mapping camera, and a computer system configured to transfer data to and from the mixed reality headset and the 3D spatial mapping camera. The system and method also include attaching a jig to a bone, mapping the bone and jig using the 3D spatial mapping camera, and then identifying a location for the surgical procedure using the computer system. Then the system and method use the mixed reality headset to provide a visualization of the location for the surgical procedure.

2 Claims, 5 Drawing Sheets

Related U.S. Application Data

No. 17/169,274, filed on Feb. 5, 2021, now abandoned, which is a continuation of application No. 17/030,351, filed on Sep. 23, 2020, now abandoned, which is a continuation of application No. 16/994,662, filed on Aug. 17, 2020.

(51) Int. Cl.

| | | |
|---|---|---|
| *A61B 34/20* | (2016.01) | |
| *A61B 90/00* | (2016.01) | |
| *A61B 90/50* | (2016.01) | |
| *A61B 90/92* | (2016.01) | |
| *G06F 3/03* | (2006.01) | |
| *G06T 7/73* | (2017.01) | |
| *G06T 19/20* | (2011.01) | |

(52) U.S. Cl.
CPC ............ *G06T 7/75* (2017.01); *G06T 19/20* (2013.01); *A61B 2034/102* (2016.02); *A61B 2034/105* (2016.02); *A61B 2034/107* (2016.02); *A61B 2034/2057* (2016.02); *A61B 2034/2065* (2016.02); *A61B 2090/365* (2016.02); *A61B 2090/373* (2016.02); *A61B 2090/3937* (2016.02); *A61B 2090/502* (2016.02); *G06T 2207/10028* (2013.01); *G06T 2210/41* (2013.01); *G06T 2219/2008* (2013.01); *G06T 2219/2012* (2013.01)

(56) References Cited

U.S. PATENT DOCUMENTS

| | | | |
|---|---|---|---|
| 8,123,754 B2 | 2/2012 | Siebel | |
| 8,560,047 B2 | 10/2013 | Haider et al. | |
| 8,876,830 B2 | 11/2014 | Hodorek | |
| 8,954,181 B2 | 2/2015 | MacLeod | |
| 8,956,165 B2 | 2/2015 | Kurenov | |
| 9,165,318 B1* | 10/2015 | Pauley | G06Q 30/0643 |
| 9,563,266 B2 | 2/2017 | Banerjee | |
| 9,730,713 B2 | 8/2017 | Park | |
| 9,861,446 B2 | 1/2018 | Lang | |
| 9,892,564 B1 | 2/2018 | Cvetko et al. | |
| 9,978,141 B2 | 5/2018 | Stolka et al. | |
| 9,980,780 B2 | 5/2018 | Lang | |
| 10,016,243 B2 | 7/2018 | Esterberg | |
| 10,108,266 B2 | 10/2018 | Banerjee | |
| 10,159,530 B2 | 12/2018 | Lang | |
| 10,194,990 B2 | 2/2019 | Amanatullah | |
| 10,220,181 B2 | 3/2019 | Giap | |
| 10,241,569 B2 | 3/2019 | Lanman | |
| 10,278,777 B1 | 5/2019 | Lang | |
| 10,285,765 B2 | 5/2019 | Sachs | |
| 10,286,179 B2 | 5/2019 | Giap | |
| 10,292,768 B2 | 5/2019 | Lang | |
| 10,368,947 B2 | 8/2019 | Lang | |
| 10,401,954 B2 | 9/2019 | Koker | |
| 10,405,873 B2 | 9/2019 | Amiot | |
| 10,405,927 B1 | 9/2019 | Lang | |
| 10,437,335 B2 | 10/2019 | Daniels | |
| 10,437,339 B2 | 10/2019 | Banerjee | |
| 10,602,114 B2 | 3/2020 | Casas | |
| 10,672,288 B2 | 6/2020 | Ribeira et al. | |
| 10,716,643 B2 | 7/2020 | Justin et al. | |
| 10,888,399 B2 | 1/2021 | Kopelman et al. | |
| 10,980,601 B2 | 4/2021 | Yang et al. | |
| 11,045,263 B1 | 6/2021 | Nevins et al. | |
| 11,172,990 B2 | 11/2021 | Lang | |
| 2005/0251030 A1 | 11/2005 | Azar et al. | |
| 2007/0270685 A1* | 11/2007 | Kang | A61B 34/76 600/424 |
| 2008/0183179 A1 | 7/2008 | Siebel | |
| 2009/0163923 A1 | 6/2009 | Flett | |
| 2014/0222462 A1 | 8/2014 | Shakil et al. | |
| 2016/0191887 A1 | 6/2016 | Casas | |
| 2017/0245781 A1 | 8/2017 | Kay | |
| 2017/0258526 A1 | 9/2017 | Lang | |
| 2017/0287218 A1* | 10/2017 | Nuernberger | G06F 3/04845 |
| 2017/0312032 A1 | 11/2017 | Amanatullah et al. | |
| 2017/0367766 A1 | 12/2017 | Mahfouz | |
| 2017/0367771 A1 | 12/2017 | Tako et al. | |
| 2018/0049622 A1 | 2/2018 | Ryan et al. | |
| 2018/0090029 A1 | 3/2018 | Fisher | |
| 2018/0098813 A1 | 4/2018 | Nesichi | |
| 2018/0116728 A1 | 5/2018 | Lang | |
| 2018/0240276 A1 | 8/2018 | He et al. | |
| 2018/0348876 A1 | 12/2018 | Banerjee | |
| 2019/0038362 A1 | 2/2019 | Nash et al. | |
| 2019/0076198 A1* | 3/2019 | Berend | A61B 17/1721 |
| 2019/0110842 A1 | 4/2019 | Lang | |
| 2019/0142520 A1 | 5/2019 | VanDyken | |
| 2019/0149797 A1 | 5/2019 | Casas | |
| 2019/0216562 A1 | 7/2019 | Sachs | |
| 2019/0262078 A1 | 8/2019 | Lang | |
| 2019/0366030 A1 | 12/2019 | Giap et al. | |
| 2019/0380792 A1 | 12/2019 | Poltaretskyi et al. | |
| 2020/0000527 A1 | 1/2020 | Cazal | |
| 2020/0037043 A1 | 1/2020 | Phillips et al. | |
| 2020/0078100 A1 | 3/2020 | Weinstein et al. | |
| 2020/0107003 A1 | 4/2020 | Phillips et al. | |
| 2020/0275976 A1 | 9/2020 | Mckinnon et al. | |
| 2020/0275988 A1 | 9/2020 | Johnson et al. | |
| 2020/0302694 A1 | 9/2020 | Flexman et al. | |
| 2020/0360093 A1 | 11/2020 | Khan et al. | |
| 2020/0375666 A1 | 12/2020 | Murphy | |
| 2021/0088811 A1* | 3/2021 | Varady | G06T 19/20 |
| 2021/0093329 A1 | 4/2021 | Poltaretskyi et al. | |
| 2021/0093391 A1 | 4/2021 | Poltaretskyi et al. | |
| 2021/0093413 A1 | 4/2021 | Poltaretskyi et al. | |
| 2021/0142508 A1* | 5/2021 | Azimi | G06T 19/006 |
| 2021/0228286 A1 | 7/2021 | Moghaddam et al. | |
| 2021/0228308 A1 | 7/2021 | Berger et al. | |
| 2021/0244481 A1 | 8/2021 | Jaramaz et al. | |
| 2022/0047279 A1 | 2/2022 | Nevins et al. | |
| 2022/0051483 A1 | 2/2022 | Nevins et al. | |

FOREIGN PATENT DOCUMENTS

| | | |
|---|---|---|
| CN | 110431636 A | 11/2019 |
| DE | 10103922 A1 | 8/2002 |
| DE | 102015212352 A1 | 1/2017 |
| EP | 3113682 A1 | 1/2017 |
| GB | 2570758 A | 7/2019 |
| JP | 2020-515891 A | 5/2020 |
| WO | 2007/108776 A2 | 9/2007 |
| WO | 2012/033739 A2 | 3/2012 |
| WO | 2015/134953 A1 | 9/2015 |
| WO | 2017/066373 A1 | 4/2017 |
| WO | 2018/007091 A1 | 1/2018 |
| WO | 2018132804 A1 | 7/2018 |
| WO | 2018/175971 A1 | 9/2018 |
| WO | 2019051080 A1 | 3/2019 |
| WO | 2019/245870 A1 | 12/2019 |
| WO | 2020033568 A2 | 2/2020 |
| WO | 2020037308 A1 | 2/2020 |
| WO | 2020047051 A1 | 3/2020 |
| WO | 2020145826 A1 | 7/2020 |
| WO | 2021094354 A1 | 5/2021 |

OTHER PUBLICATIONS

Kaluschke et al., HIPS—A Virtual Reality Hip Prosthesis Implantation Simulator, retrieved at https://www.reasearchgate.net/publication/327329265, upload date Sep. 3, 2018 DOI: 10.1109/VR.2018.8446370.

Vaughan et al., Does Virtual-Reality Training on Orthopaedic Simulators Improve Performance in the Operating Room? Science and Information Conference 2015, Jul. 28-30, 2015, London, UK; retrieved at https://www.researchgate.net/publication/284415791; DOI: 10.1109/SAI.2015.7237125.

Patently Apple—Apple Reveals a Mixed Reality Headset that Uses a Direct Retinal Projector System With Holographic Lenses, retrieved

(56) References Cited

OTHER PUBLICATIONS at https://www.patentlyapple.com/patently-apple/2019/09/apple-reveals-a-mixed-reality-headset-that-uses-a-direct-retinal-projector-system-with-hologra . . . ; posted date Sep. 19, 2019.

Virtual Reality System Helps Surgeons, Reassures Patients, retrieved at https//medicalgiving.stanford.edu/news/virtual-reality-system-helps-surgeons-reassures-patients.html, retrieved date Oct. 24, 2019.

Immersive Touch Launches the First Virtual Reality Integrated Suite for Surgical Planning, retrieved at https://spinalnewsinternational.com/immersivetouch-virtual-reality-suite, dated Oct. 5, 2018.

Daley, Sam, The Cutting Edge: 10 Companies Bringing Virtual Reality & AR to the OR, retrieved at https://builtin.com/healthcare-technology/augmented-virtual-reality-surgery, dated Jul. 5, 2019.

Barad, Justin, Virtual and Augmented Reality Can Save Lives by Improving Surgeons' Training, retrieved at https://www.statnews.com/2019/08/16/virtual-reality-improve-surgeon-training, dated Aug. 16, 2019.

Levin et al., The Future of Virtual Reality in Ophthalmology Is Already Here, retrieved at https://www.aao.org/young-ophthalmologists/yo-info/article/future-of-virtual-reality-in-ophthalmology, dated Aug. 16, 2019.

Vaughan et al., A Review of Virtual Reality Based Training Simulators for Orthopaedic Surgery, retrieved at https://www.researchgate.net/publication/283727217, posted date Feb. 22, 2019, DOI: 10.1016/j.medengphy.2015.11.021.

LexInnova Patent Landscape Analysis, Virtual Reality, unknown author, copyright date of 2015.

Virtual & Augmented Reality Are You Sure it Isn't Real? Kathleen Boyle, CFA, Managing Editor, Citi GPS dated Oct. 2016.

New Apple patent filing shows a mixed reality headset that tracks your whole face, Jul. 22, 2019, (downloaded Jul. 1, 2020 at https://www.theverge.com/2019/7/22/20705158/apple-mixed-reality-headset-ar-glasses-patent-application-face-tracking), 2 pages.

"Augmented and virtual reality in surgery—the digital surgical environment: application, limitations and legal pitfalls," accessed at https://www.ncbi.nlm.nih.gov/pmc/articles/PMC5220044/, visited on Jul. 4, 2020. 12 pages.

"The impact of Web3D technologies on medical education and training," Science Direct, accessed at https://www.sciencedirect.com/science/article/pii/S0360131505000825, visited on Jul. 4, 2020, 11 pages.

"Mixed Reality with HoloLens: Where Virtual Reality Meets Augmented Reality in the Operating Room," accessed at https://www.ingentaconnect.com/content/wk/prs/2017/00000140/00000005/art00063, visited on Jul. 4, 2020, 1 page.

"Virtual Reality Simulation in Neurosurgery: Technologies and Evolution," Abstract, accessed at https://academic.oup.com/neurosurgery/article-abstract/72/suppl_1/A154/2417686, visited on Jul. 4, 2020, 2 pages.

Katanacho, Manuel, Wladimir De la Cadena, and Sebastian Engel. "Surgical navigation with QR codes: Marker detection and pose estimation of QR code markers for surgical navigation." Current Directions in Biomedical Engineering 2.1 (2016): 355-358.

\* cited by examiner

SYSTEM AND METHOD FOR LOCATION DETERMINATION USING A MIXED REALITY DEVICE AND A 3D SPATIAL MAPPING CAMERA

CROSS-REFERENCE TO RELATED APPLICATIONS

This application is a continuation of non-provisional U.S. patent application Ser. No. 17/473,867, filed on Sep. 13, 2021, which is a continuation of non-provisional U.S. patent application Ser. No. 17/169,274, filed on Feb. 5, 2021, which is a continuation of non-provisional U.S. patent application Ser. No. 17/030,351, filed on Sep. 23, 2020, which is a continuation of non-provisional U.S. patent application Ser. No. 16/994,662, filed on Aug. 17, 2020, which are hereby incorporated by reference herein in their entirety, including but not limited to those portions that specifically appear hereinafter, the incorporation by reference being made with the following exception: in the event that any portion of the above-referenced applications are inconsistent with this application, this application superseded said above-referenced applications.

STATEMENT REGARDING FEDERALLY SPONSORED RESEARCH OR DEVELOPMENT

Not applicable.

BACKGROUND

1. The Field of the Present Disclosure

The present disclosure relates generally to surgical systems and methods of facilitating the efficiency and accuracy of implanting surgical prostheses using mixed reality and 3D spacial mapping devices.

2. Description of Related Art

In traditional implant surgeries, for example, knee replacements, a surgeon will utilize a metal jig which is used as a drilling or cutting guide to make the necessary corresponding cuts and holes in the bone of the knee to facilitate placement and attachment of the implant to the bone. However, these metal jigs must be stocked in a variety of different sizes to accommodate different needs and sizes of patients, accordingly, significant stocks of metal jigs must be stored and sterilize. Additionally, use of these metal jigs include inherent inaccuracies as the surgeons fix the metal jigs with respect to the corresponding bone during use as a drill or cutting guide.

The femoral implant and tibial implant are designed to be surgically implanted into the distal end of the femur and the proximal end of the tibia, respectively. The femoral implant is further designed to cooperate with the tibial implant in simulating the articulating motion of an anatomical knee joint.

These femoral and tibial implants, in combination with ligaments and muscles, attempt to duplicate natural knee motion as well as absorb and control forces generated during the range of flexion. In some instances however, it may be necessary to replace or modify an existing femoral and/or tibial implant. Such replacements are generally referred to as revision implants.

To prepare a femur and tibia for such a knee replacement and form an engagement with femoral and tibial implants, the femur and tibia bones must be cut in very specific and precise ways and at very specific and precise angles and locations, so that the prepared bone will properly engage with and be secured to the corresponding implants. In order to make these cuts properly, a surgeon traditionally uses a jig, or surgical cutting guide as known to those skilled in the field, which can be removably attached or secured to the bone, such that slots, or guides, in the jig facilitate the precise cuts necessary to secure the corresponding implants.

The phrase "jig" as used herein, shall thus refer broadly to a surgical cutting guide, that may be configured and arranged to be fixed or attached to a bone, or secured adjacent to a bone or other tissue to be cut by a surgeon and identify a relative location, angle and/or cutting plane that a surgeon should cut or drill on the adjacent bone or tissue, as known in the art. A jig may include predetermined slots and/or cutting surfaces to identify where a surgeon should cut the adjacent bone or tissue, wherein such cuts may correspond to a shape of a surgical implant that may be attached to the cut bone or tissue. A "cutting surface" may refer to a guide edge for guiding the path of a cutting instrument.

Conventional jigs are typically made of a metal alloy and, due to the precise tolerances at which these jigs must be machined, are quite expensive, ranging as high as $40,000-$50,000 in some cases. These metal jigs must also be stored and reused, which adds additional cost and space resources. Additionally, jigs of various sizes must be kept on had to accommodate patients of different sizes and needs.

Therefore, there is a need for a system that can utilize a less expensive jig, such as a plastic jig, that could be made easily and on demand, while maintaining the required tolerances and enable the same accuracy in use in a surgical procedure.

In other conventional embodiments, holographic jigs, also referred to a virtual jigs, have been used to enable a surgeon to visualize the positioning and proper sizing of a jig to a bone. However, in use, when the surgeon attempts to superimpose a physical jig over the virtual jig to attach it to a bone to make the required bone cuts, the physical jig will impair the view of the virtual or holographic jig, making it difficult to utilize the holographic jig to accurately place the physical jig.

Accordingly, there is a need for a system and method of utilizing a virtual or holographic jig or surgical instrument that could facilitate increased accuracy and precision of required or desired bone cuts.

The phrase "virtual jig" or "holographic jig" as used herein, shall thus refer broadly to any visualization or visual rendering or projection representing an actual physical jig, having all, or mostly all, of the same visual characteristics of the physical jig, including size and shape, as known in the art.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims. Any discussion of documents, acts, materials, devices, articles or the like which has been included in the present specification is not to be taken as an admission that any or all of these matters form part of the prior art base, or were common general knowledge in the field relevant to the present disclosure as it existed before the priority date of each claim of this application.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
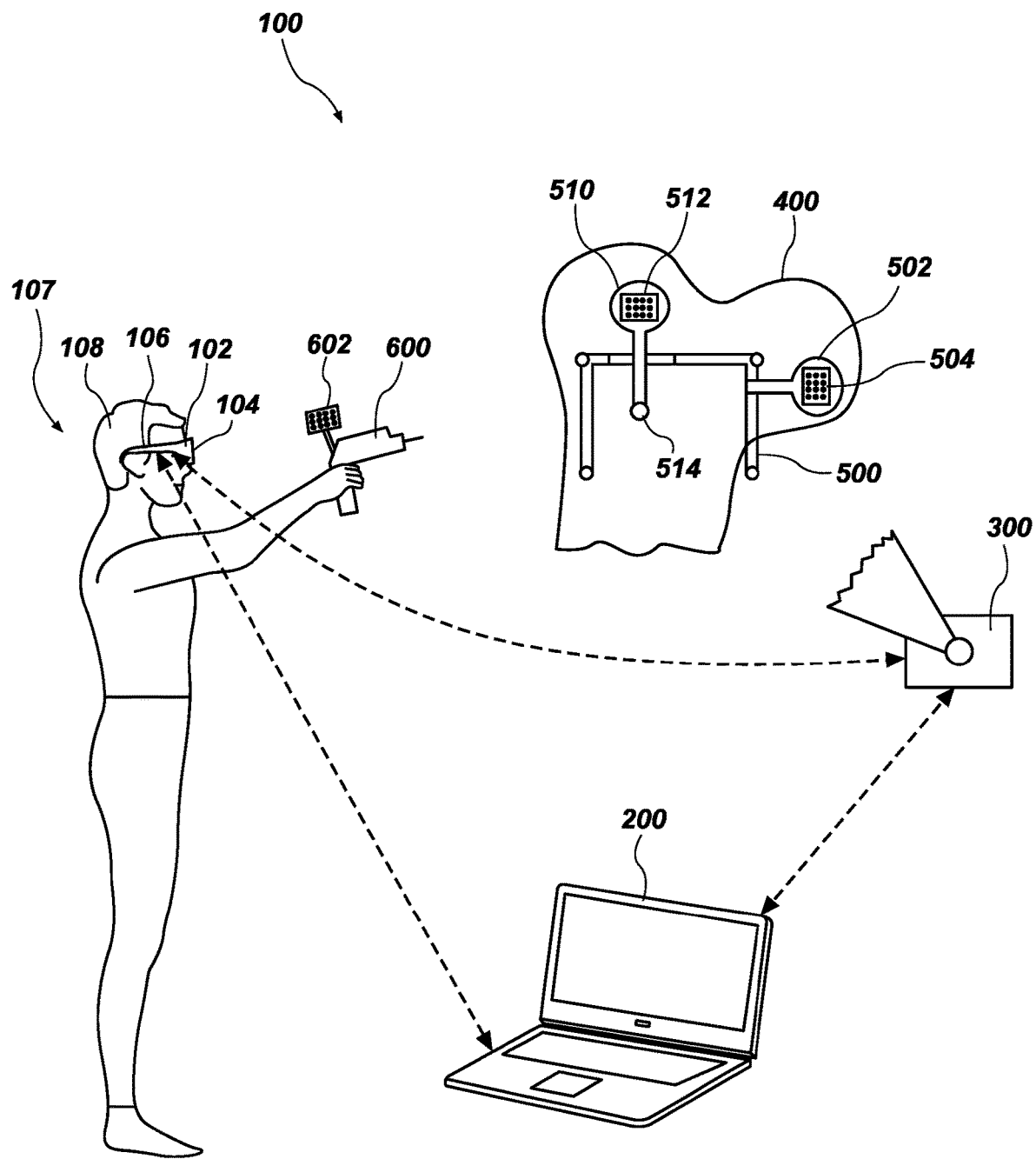
FIG. 1 is a schematic rendering of a mixed reality system of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the terms "virtual," and "hologram" are used interchangeably, and grammatical equivalents thereof are inclusive or open-ended terms that do not exclude additional, unrecited elements or method steps. These terms are used to describe visual representations of an actual physical device or element, having all, or mostly all, of the same visual characteristics of the physical device, including size and shape.

Applicant has discovered a novel system and method for generating and using a virtual jig, or virtual instrument, in a surgical procedure, for example, in a knee or tibial implant procedure, or other desired surgical procedure.

The phrase "virtual system" as used herein, shall refer broadly to any system capable of generating or creating a simulated or virtual rendering or projection of physical or structural features identical or substantially identical to an actual physical device, instrument or other physical structure, as known in the art. A virtual system may also include a device, mechanism, or instrument capable of projecting or displaying the desired a simulated or virtual rendering or projection of physical or structural features identical or substantially identical to an actual physical device. A virtual system may also enable a user to manipulate, move and/or modify the simulated or virtual rendering or projection.

The phrase "mixed or augmented reality system" as used herein, shall refer broadly to any system capable of generating or creating a simulated or virtual rendering or projection of physical or structural features identical or substantially identical to an actual physical device, instrument or other physical structure, as known in the art. A mixed or augmented reality system may also include a device, mechanism, or instrument capable of projecting or displaying the desired a simulated or virtual rendering or projection of physical or structural features identical or substantially identical to an actual physical device overlaid or concurrently with actual physical structures, mechanism or devices in reality, thus incorporating the virtual rendering or projection in real world settings with actual physical element. A mixed or augmented reality system may also enable a user to manipulate, move and/or modify the simulated or virtual rendering or projection.

The phrase "mixed or augmented reality instrument" as used herein, shall refer broadly to any device, mechanism or instrument used in a mixed or augmented reality system, including a device capable of generating or creating a simulated or virtual rendering or projection of physical or structural features identical or substantially identical to an actual physical device, instrument or other physical structure, as known in the art. A mixed or augmented reality instrument may also be capable of projecting or displaying the desired a simulated or virtual rendering or projection of physical or structural features identical or substantially identical to an actual physical device overlaid or concurrently with actual physical structures, mechanism or devices in reality, thus incorporating the virtual rendering or projection in real world settings with actual physical element. A mixed or augmented reality instrument may also enable a user to manipulate, move and/or modify the simulated or virtual rendering or projection.

The phrase "holographic representation" as used herein, shall refer broadly to a visualization or visual rendering or projection representing an actual physical device or element, having all, or mostly all, of the same visual characteristics of the corresponding physical device or element, including size and shape, as known in the art.

Referring to FIG. 1, in a disclosed embodiment a mixed or augmented system 100, which can be used to produce, or display, a desired mixed or augmented reality instrument, such as a virtual jig or cutting guide in a display to a surgeon or user, or stated another way, that is visible and manipulatable by a surgeon or user. The mixed or augmented reality system 100 may also enable a user to activate or deactivate, in full or in part, the virtual instrument or instruments, making a virtual instrument appear or disappear, as desired in a mixed reality assisted surgery, for example.

The mixed or augmented reality system 100 may include a mixed or augmented reality headset 102 which may include a transparent or mostly transparent viewer 104 which can be suspended or positioned in front of a user's eyes. The headset 102 may include a headband 106 attached to the viewer 104, which may be used to secure the headset 102 to a user's head 108, thereby securing the viewer 104 in place in front of the user's eyes.

The transparent viewer 104 may be configured to project, or otherwise make viewable, on an interior surface of the viewer 104, a holographic image or images, such as a virtual device, for example, a virtual cutting guide, which may be positionally manipulated by the user, surgeon, third party or remote system, such as a remote computer system. The headset 102 may be configured to view holographic images or, alternatively, the holographic images may be turned off and the user wearing the headset 102 may be able to view the surrounding environment through the transparent viewer 104, unobstructed. As such, a user, such as a surgeon for example, can wear the mixed or augmented reality headset 102 and then can choose to activate a holographic image to aide in facilitating a surgical procedure and then shut off the holographic image in order to perform the surgical procedure un-obscured, visually.

One embodiment of the disclosed headset 102 may be a product created and manufactured by Microsoft, known as the HoloLens® mixed or augmented reality system, or any suitable mixed or augmented reality system for generating virtual images viewable by a user or surgeon. Headset 102 may be a conventional "off the shelf" product with a built-in platform that enables all of the features described herein with respect to the headset 102. Furthermore, the headset 102, such as a Microsoft HoloLens product, can be loaded or preloaded with all desired or required virtual instruments, including virtual jigs or surgical cutting guides, virtual drill bits, and/or a virtual target which can identify relative locations of a plurality of holes to be drilled by a surgeon to facilitate the fastening of a jig or other device onto a desired bone at the proper desired location, and any other desired virtual instruments or holograms. The Microsoft HoloLens product and its capabilities and features, or any suitable mixed or augmented reality system such as is described herein with respect to the headset 102, are known to those skilled in the art.

The mixed reality system 100 may also include a computer or computer system 200 having enabling software to communicate with the headset 102, by both receiving information from the headset 102 and transmitting data and images to the headset 102. It is therefore to be understood, by way of the circuit diagram and dashed lines shown in FIG. 1, that headset 102 is electronically connected to the computer system 200 and a 3D spatial mapping camera 300. The 3D spatial mapping camera 300 is electronically connected to the headset 102 and the computer system 200, as shown in the circuit diagram and dashed lines shown in FIG. 1. While the 3D spatial mapping camera 300 may be electronically connected to the headset 102, the 3D spatial mapping camera 300 may be separate from and not mechanically connected to the headset 102.

The mixed reality system 100 may also include a 3D spatial mapping camera 300. One embodiment of the disclosed spatial mapping camera 300 may be a product created and manufactured by Microsoft, known as the Azure Kinect®, or any suitable 3D spatial mapping camera capable of continuous 3D mapping and transition corresponding 3D images, such as bones, anatomy, or other desired 3D objects. The spatial mapping camera 300 may be a conventional "off the shelf" product with a built-in platform that enables all of the features described herein with respect to the spatial mapping camera 200. Furthermore, the spatial mapping camera 200, such as a Microsoft Azure Kinect product, can be loaded or preloaded with all necessary software to enable wireless communication between the spatial mapping camera 300 and the computer system 200 and/or the headset 102. The Microsoft Azure Kinect product and its capabilities and features, or any suitable 3D spatial mapping camera such as is described herein with respect to the spatial mapping camera 300, are known to those skilled in the art.

The spatial mapping camera 300 may include sensor software development kits for low-level sensor and device access, body tracking software development kits for tracking bodies or objects in 3D, and speech cognitive services software development kits for enabling microphone access and cloud-based or wireless speech services.

Additionally, the spatial mapping camera 300 may include the following features: depth camera access and mode control (a passive IR mode, plus wide and narrow field-of-view depth modes); RGB camera access and control (for example, exposure and white balance); a motion sensor (gyroscope and accelerometer) access; synchronized depth-RGB camera streaming with configurable delay between cameras; external device synchronization control with configurable delay offset between devices; camera frame metadata access for image resolution, timestamp, etc.; and device calibration data access.

The spatial mapping camera 300 may also include software development kits that enable a viewer tool to monitor device data streams and configure different modes; a sensor recording tool and playback reader API that uses the Matroska container format, as known to those of ordinary skill in the field; a library and runtime to track bodies in 3D when used with the spatial mapping camera 300; contains an anatomically correct skeleton for each partial or full body; provides a unique identity for each body; can track bodies over time; and speech services, such as, speech-to-text, speech translation and text-to-speech.

The headset 102, computer system 200 and spatial mapping camera 300, may be programmed and configured to enable a surgeon 107 to see and manipulate a virtual, or holographic target or jig, with respect a patient's bone 400, anatomical, or any other desired location, which may receive a surgical implant. The headset 102, computer system 200 and spatial mapping camera 300 may communicate with one another via a local network connection, wifi, bluetooth, or any other known wireless communication signal.

Specifically, the spatial mapping camera 300, that may be programed to communicate with the computer system 200 having enabling software, may utilize such enabling software to map the bone 400 and or jig 500, or other desired anatomy, to help identify the proper location for fastening a jig, or other device, to the bone 400, prior to cutting the knee.

The spatial mapping camera 300 differs from traditional imaging, such as an MRI, CT scan, x-ray or the like, in many ways. For example, the spacial mapping camera 300 may be mounted, fixedly or moveably, in an operating room, thus giving the most up-to-date mapping information possible. The spatial mapping camera 300 may also continuously map the surface and 3D contours of the bone 400 to provide the surgeon 107 with realtime feedback and information to make the proper drill holes, cuts, or other preparations on the bone 400, before, during, and/or after any given procedure.

The mixed reality system 100 may also include an alignment jig 500 that can be secured to the exposed bone 400, or other desired anatomy. The jig 500 may includes a first marker 502 which may be attached to the jig 500 at a fixed location on the bone 400. The first marker 502 may include a scannable, optical or visual label 404, such as a QR code. The jig 500 may also include a second marker 510 that may be moveable with respect to the jig 500 and the bone 400. The second marker 510 may also include a scannable, optical or visual label 412, such as a QR code.

The mixed reality system 100 may also include a surgical tool 600, such as a drill for example, that may also include a scannable label 602, such as a QR code, which can be scanned by the headset 102 and or spatial mapping camera 300, which may include data related to the jig 500, surgical procedure, and/or the corresponding patient. This data may be transmitted and processed by the computer system 200, which may then prompt or identify to the surgeon 107, via the headset 102 where, and at what angle, to position the tool 600 to drill, cut, or otherwise prepare the bone 400, at the proper location on the bone 400.

Figure 2:
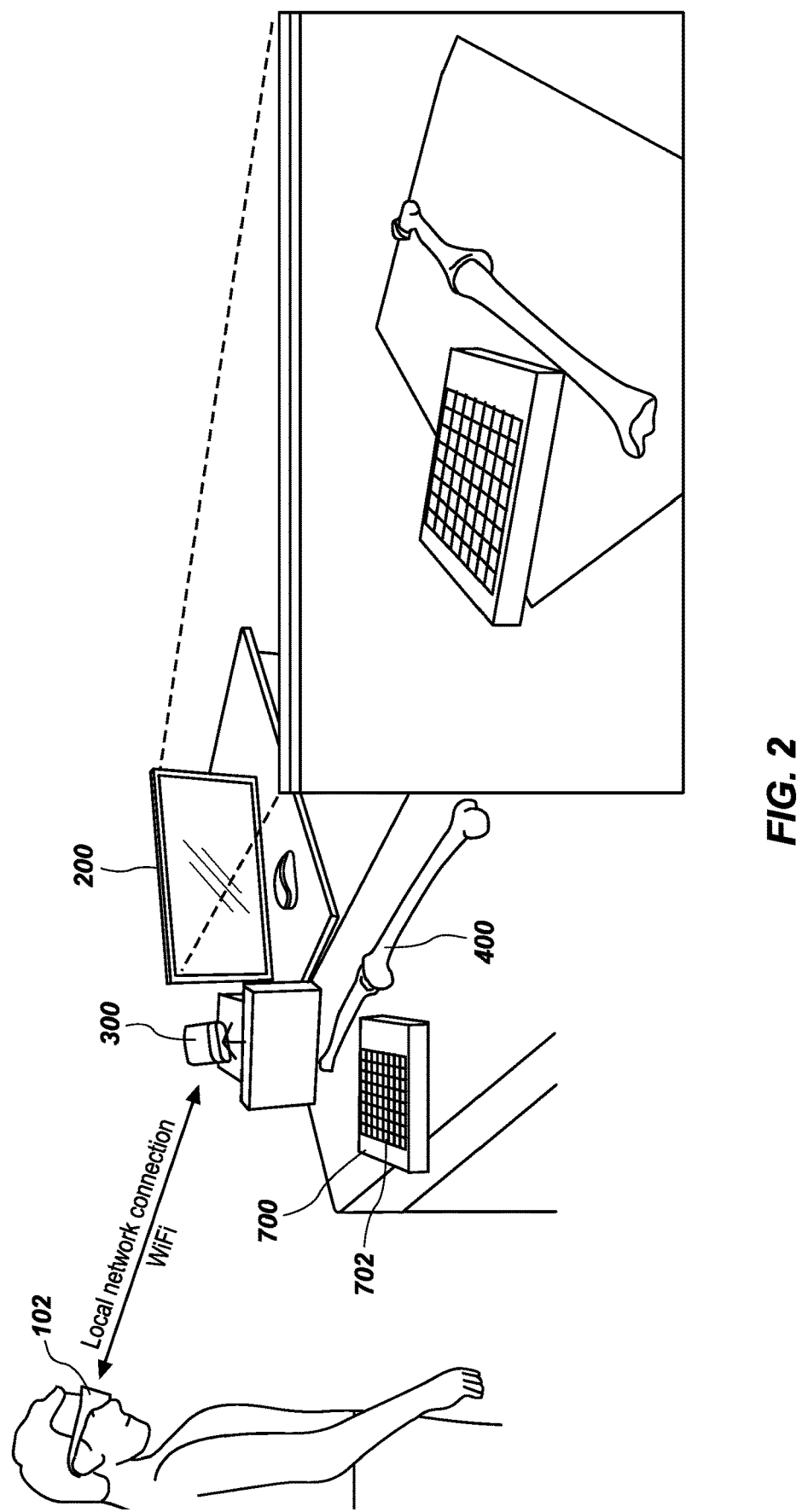
FIG. 2 is a perspective view of another embodiment of a mixed reality system of the present disclosure.

In another embodiment, as shown in FIG. 2, the headset 102 and the spatial mapping camera 300 may utilize a physical calibration tool 700 to calibrate and align 3D coordinates with the 3D contours of the exposed bone 400 or anatomy. The calibration tool 700 may include a specially designed calibration pattern 702 than may be scanned by the headset 102 and/or the spatial mapping camera 300, which can then send the corresponding calibration data to the computer system 200 which can then use the calibration data to provide accurate coordinates to the headset 102 to identify where to drill, cut, or otherwise prepare the bone 400.

Figure 3:
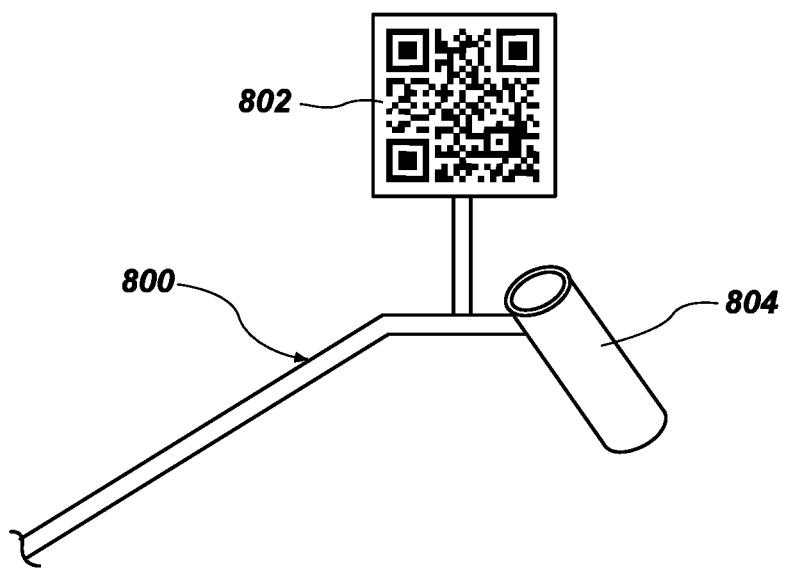
FIG. 3 is a side view of a pin guide of the present disclosure.

In a further embodiment, as shown in FIG. 3, the mixed reality system 100 may also include a pin guide 800 that may also include a scannable label 802, such as a QR code, which can be scanned by the headset 102, which may then prompt or identify to the surgeon 107 where, and at what angle, to position the pin guide 800 to perform a desired procedure, at the proper location on the bone 400. The pin guide 800 may also include a guide sleeve 804 which can provide a directional guide to receive and orient a pin (not shown) to be placed by the surgeon during a procedure. the surgeon to drill, cut, or otherwise prepare the bone 400.

Using the mixed reality system 100, a surgeon or user may perform a surgical procedure by first exposing the bone 400, or other desired anatomy. The spatial mapping camera 300 may then continuously 3D spatially map the exposed bone 400, and send the corresponding mapping information to the computer system 200. In alternative embodiments multiple spatial mapping cameras 300 may be used in unison, to provide more accurate and expansive imaging.

The surgeon may then attach the jig 500 to the exposed bone 400, at a predetermined or desired location. The spatial mapping camera 300 may spatially map the jig 500 and the exposed bone 400, to map the surface of the exposed bone and relative location of the jig 500.

The surgeon may then utilize the headset 102 or spatial mapping camera 300 to scan the fixed scannable label 504 of the first marker 502 and send the corresponding information to the computer system 200. The computer system 200 may then utilize data from the 3D spatial mapping camera 300 and the scannable label 502 of the first marker 502 to determine the orientation of the moveable second marker 510 and send the data to the headset 100.

Figure 4:
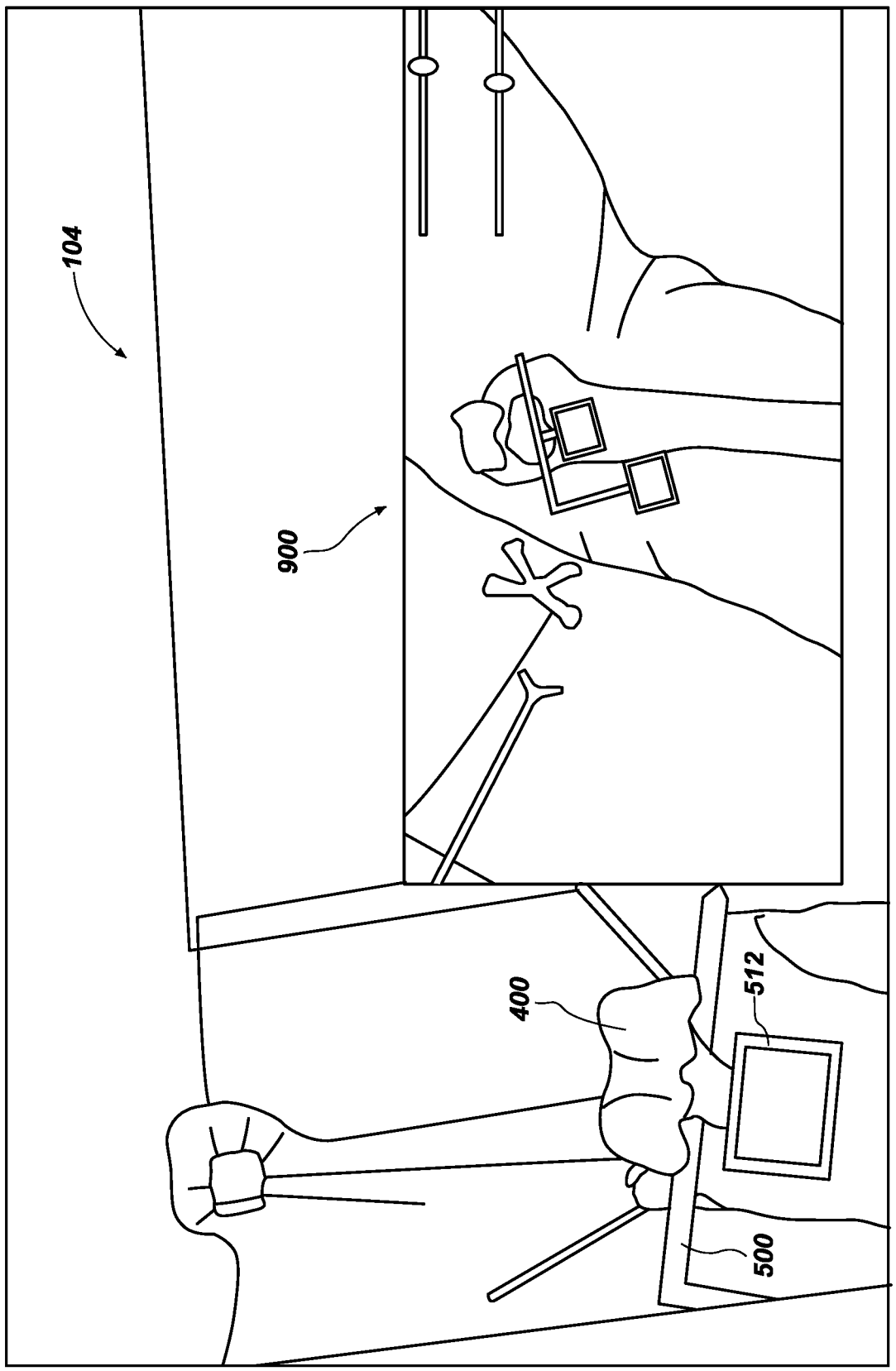
FIG. 4 is a front view of a user perspective of a mixed reality headset viewer of the present disclosure.

As shown in FIG. 4, the headset 102 may generate a holographic image 900, or visualization, viewable by the surgeon on the viewer 104, such that the surgeon can maintain a real-world view of the bone 400 and simultaneously view the holographic image 900. The holographic image 900 may include a realtime rendering of the exposed bone 400 and a realtime rendering of the jig 500. The headset 102 can then scan the scannable label 512 of the second marker 510 and identify the proper or required position of the second marker 510, relative to the bone 400. This identified position of the second marker 510 may be viewed by the surgeon in holographic image 900. The surgeon can then manipulate the rendering of the second marker 510 in the holographic image 900, until the proper position is set and determined.

Once the proper position of the second marker 510 is set in the holographic image 900 the surgeon can use the headset 102 to lock the holographic image 900 in place. Then the surgeon can manipulate the actual physical second marker 510 to substantially match the positioning of the set rendering of the second marker 510. A target 514 located on the second marker 510 may provide the surgeon with the substantially exact location to drill a required hole, or place a pin, with respect to the exposed bone 400, such that the surgeon can manipulate the location of the jig with respect to the bone 400, to substantially match the location of the virtual jig, or holographic image 900, with respect to a virtual bone.

The headset 102 may help facilitate the proper orientation of the second marker 510, and corresponding target 514, by illuminating the target 514 or by providing a colored symbol, either of which may include a color, such as red, that may change colors, such as changing from red to green, when the target is ultimately moved into the proper position, by operation of a microprocessor (not shown) contained within headset 102 or computer system 200, said processor being programed as known to those skilled in the art of programming to trigger a change of color when the target is moved into the proper position.

Figure 6:
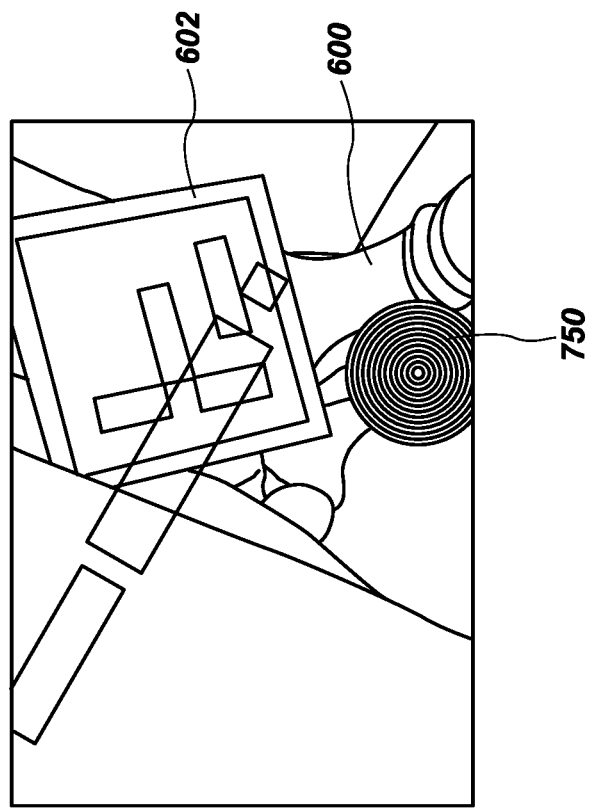
FIG. 6 is a front view of a further user perspective of a mixed reality headset viewer, during a procedure, of the present disclosure.
Figure 5:
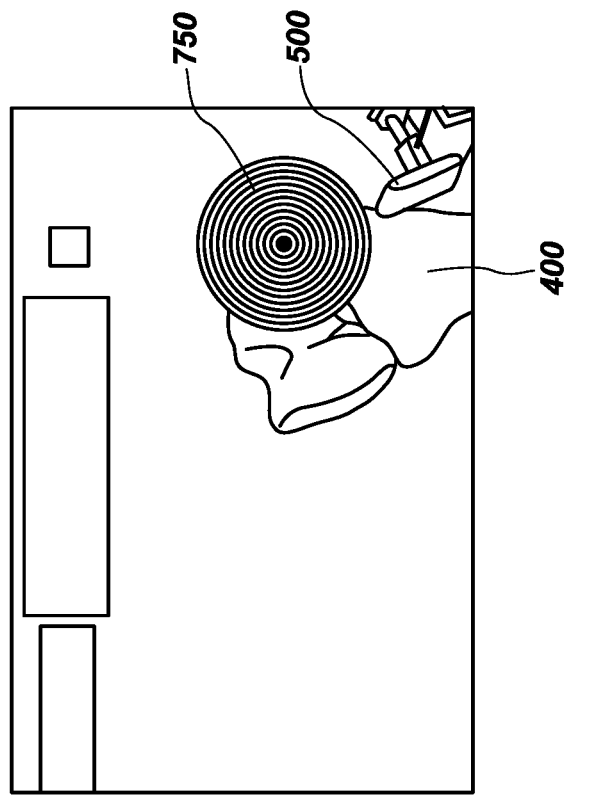
FIG. 5 is a front view of another user perspective of a mixed reality headset viewer, during a procedure, of the present disclosure.

As shown in FIGS. 5 and 6, the headset 102 may then scan the scannable label 602 of tool 600 or scannable label 802 of pin guide 800 and identify the location and angle of the tool 600 or pin guide 800, to make the required drill hole, or pin insertion. The headset 102 may help facilitate the proper orientation of the tool 600 or pin guide 800, by providing a colored symbol 750, such as red, that may change colors, such as green, when the tool 600 or pin guide 800 are ultimately moved into the proper position. The surgeon may then use the properly oriented tool 600 or pin guide 800 to perform the corresponding procedure or preparation of the bone 400. A cutting jig (not shown) may then be attached to the bone 400 at the prepared position.

A surgical jig is conventionally, and may be, a surgical tool that may be used to help a surgeon make predetermined and accurate cuts of a desired bone to facilitate attachment of a surgical implant. A jig may have one or a series of slots located at specific predetermined locations and at specific predetermined angles, with respect to a body of the jig, such that when the jig is attached to a bone surface, the surgeon can make precise and accurate cuts, using the jig as a guide, without the need of additional measurements. Once the desired cuts of the bone have been made using the jig as a guide, the jig may be removed from the bone and the surgical implant may be properly secured to the bone which has now been accurately cut to receive the implant.

Due to the accuracy of the disclosed method and system, the jig 500 may be made of plastic, metal, polyamide, or any other desired material. Manufacturing the jig 500 out of a plastic or polyamide material, or other relatively inexpensive material, may allow the jig 500 to be disposable, while still maintaining the precision and accuracy of traditional metal jigs. The jig 500 may also be manufactured using a 3D printer, which can further reduce the cost of manufacturing and storage of jigs, since 3D printed jigs could be made on demand, customized to the size and shape required by individual patients and users. The physical jig 500 may also be manufactured using any other known technique for forming a physical jig.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment.

Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A method for determining a location for a surgical jig in a surgical procedure, comprising:
   providing a mixed reality headset;
   providing a 3D spatial mapping camera;
   providing a computer system configured to transfer data to and from the mixed reality headset and the 3D spatial mapping camera;
   attaching a jig to a bone;
   mapping the bone and jig using the 3D spatial mapping camera;
   identifying a location for the surgical procedure using the computer system;
   using the mixed reality headset to provide a visualization of the location for the surgical procedure;
   using the mixed reality headset to provide a virtual jig and a virtual bone, which are representations of the jig and bone;
   manipulating the location of the virtual jig as viewed in the mixed reality headset, with respect to the virtual bone, thereby changing the position of the virtual jig independent of the bone;
   locking the location of the virtual jig as viewed in the mixed reality headset, with respect to the virtual bone, such that the virtual jig will remain in position, with respect to the bone, if the bone is moved;
   wherein the jig includes a visual label, wherein the visual label is configured to be scanned by the mixed reality headset to provide data relating to the jig;
   scanning the visual label of the jig using the mixed reality headset;
   identifying a position of the jig with respect to the bone based, at least in part, on the data provided by scanning the visual label;
   wherein the identifying a position of the jig includes, the mixed reality headset providing a visual target that illuminates when the jig is positioned in a correct location;
   wherein the illumination of the visual target includes the visual target changing colors;
   manipulating the location of the jig with respect to the bone, to match the location of the virtual jig with respect to the virtual bone;
   providing a tool having a visual label, wherein the visual label is configured to be scanned by the mixed reality headset to provide data relating to the tool;
   scanning the visual label of the tool using the mixed reality headset;
   identifying a position of the tool with respect to the jig and the bone based, at least in part, on the data provided by scanning the visual label of the tool;
   wherein the identifying a position of the tool includes, the mixed reality headset providing a visual target that illuminates when the tool is positioned in a correct location;
   wherein the illumination of the visual target includes the visual target changing colors; and
   wherein the mixed reality headset is separate and not mechanically connected to the 3D spatial mapping camera.

2. A method for determining a location for a surgical jig in a surgical procedure, comprising:
   providing a mixed reality headset;
   providing a 3D spatial mapping camera;
   providing a computer system configured to transfer data to and from the mixed reality headset and the 3D spatial mapping camera;
   attaching a jig to a bone, wherein the jig includes a visual label, wherein the visual label is configured to be scanned by the mixed reality headset to provide data relating to the jig;
   mapping the bone and jig using the 3D spatial mapping camera;
   identifying a location for the surgical procedure using the computer system;
   using the mixed reality headset to provide a visualization of the location for the surgical procedure; and
   using the mixed reality headset to provide a virtual jig, which is a representation of the jig;
   manipulating the location of the virtual jig as viewed in the mixed reality headset, with respect to the bone, thereby changing the position of the virtual jig independent of the bone;
   locking in the position of the virtual jig with respect to the bone;
   scanning the visual label of the jig using the mixed reality headset; and
   identifying a position of the jig with respect to the bone based, at least in part, on the data provided by scanning the visual label, wherein the identifying a position of the jig includes, the mixed reality headset providing a visual target that illuminates when the jig is positioned in a correct location, wherein the illumination of the visual target includes the visual target changing colors.

* * * * *